(12) United States Patent
Wahidullah et al.

(10) Patent No.: US 6,777,004 B1
(45) Date of Patent: Aug. 17, 2004

(54) COMPOSITION CONTAINING NOVEL COMPOUND CORNICULATONIN HAVING ANTIFUNGI PROPERTIES AND A PROCESS FOR PREPARING THE SAME

(75) Inventors: Solimabi Wahidullah, Goa (IN);
Siddharth Hariba Bhosak, Goa (IN);
Maria Lisette De Lumen D'Souza, Goa (IN)

(73) Assignee: Council of Scientific & Industrial Research, New Delhi (IN)

( * ) Notice: Subject to any disclaimer, the term of this patent is extended or adjusted under 35 U.S.C. 154(b) by 45 days.

(21) Appl. No.: 09/821,949

(22) Filed: Mar. 30, 2001

(51) Int. Cl.[7] .................. A01N 65/00; A01N 43/04; A61K 35/78; A61K 31/70; A61K 38/00
(52) U.S. Cl. .................. 424/725; 424/727; 424/750; 424/757; 514/2; 514/8; 514/12; 514/23; 514/24; 514/25; 514/183; 536/4.1
(58) Field of Search ................ 424/725, 727, 424/750, 757, 724; 514/2, 8, 12, 23, 24, 25; 536/4.1

(56) References Cited

U.S. PATENT DOCUMENTS

| | | | |
|---|---|---|---|
| 6,326,507 B1 | * | 12/2001 | Gribble et al. |
| 6,444,233 B1 | * | 9/2002 | Arntzen et al. ............. 424/725 |
| 6,689,398 B2 | * | 2/2004 | Haridas et al. ............. 424/757 |
| 2003/0054052 A1 | * | 3/2003 | Haridas et al. ............. 424/757 |

FOREIGN PATENT DOCUMENTS

WO   WO 02/077008 A1  * 10/2002

OTHER PUBLICATIONS

Field et al, Tasks for Vegetation Sciences 9:37–42, 1984.*
Subramonia Thangam et al Tropical Biomedicine 10:125–128, 1992.*
Bhosale et al, Mycopathologia 147:133–138, 1999.*
Ohtani et al, Phytochemistry 33/1:83–86, 1993.*
Kohda et al, Chem. Pharm. Bull. 37/12:3304–05, 1989.*
Podolak et al Phytotherapy Research 12:S70–S73, 1998.*
Bloor, J. Natural Products, 57/10:1354–1360, 1994.*
Hedge et al, J. Natural Products, 58/10:1492–1497, 1995.*
Thangam et al, International J. Pharmacognosy 35/1:69–71, 1997.*
Gomez et al, J. Natural Products 52/3:649–51, 1989.*
Sarma et al, Fungal Diversity, Feb. 2001, 6:115–130.*
Thangam et al, Tropical Biomedicine, 1992, 10:125–128.*

* cited by examiner

*Primary Examiner*—N. M. Minnifield
(74) *Attorney, Agent, or Firm*—McDonnell, Boehnen, Hulbert & Berghoff (57) ABSTRACT

The invention relates to a novel compound oleanane triterpenoid oligoglycoside of formula 1 of the accompanying drawing (trivially called corniculatonin), the invention also relates to a process for the isolation of the novel compound from a mangrove plant *Aegiceras corniculatum* (Blanco) belonging to the family Myrsinaceae, it also discloses the antifungal properties of the said compound, the invention further relates to the use of the said compound as a food preservative, it further discloses a composition containing effective amount of the said compound for the treatment of fungi infections.

11 Claims, 11 Drawing Sheets

Wherein $R_1$ = -OH, -OAc, and =O and

COMPOSITION CONTAINING NOVEL COMPOUND CORNICULATONIN HAVING ANTIFUNGI PROPERTIES AND A PROCESS FOR PREPARING THE SAME

FIELD OF INVENTION

Figure 1:
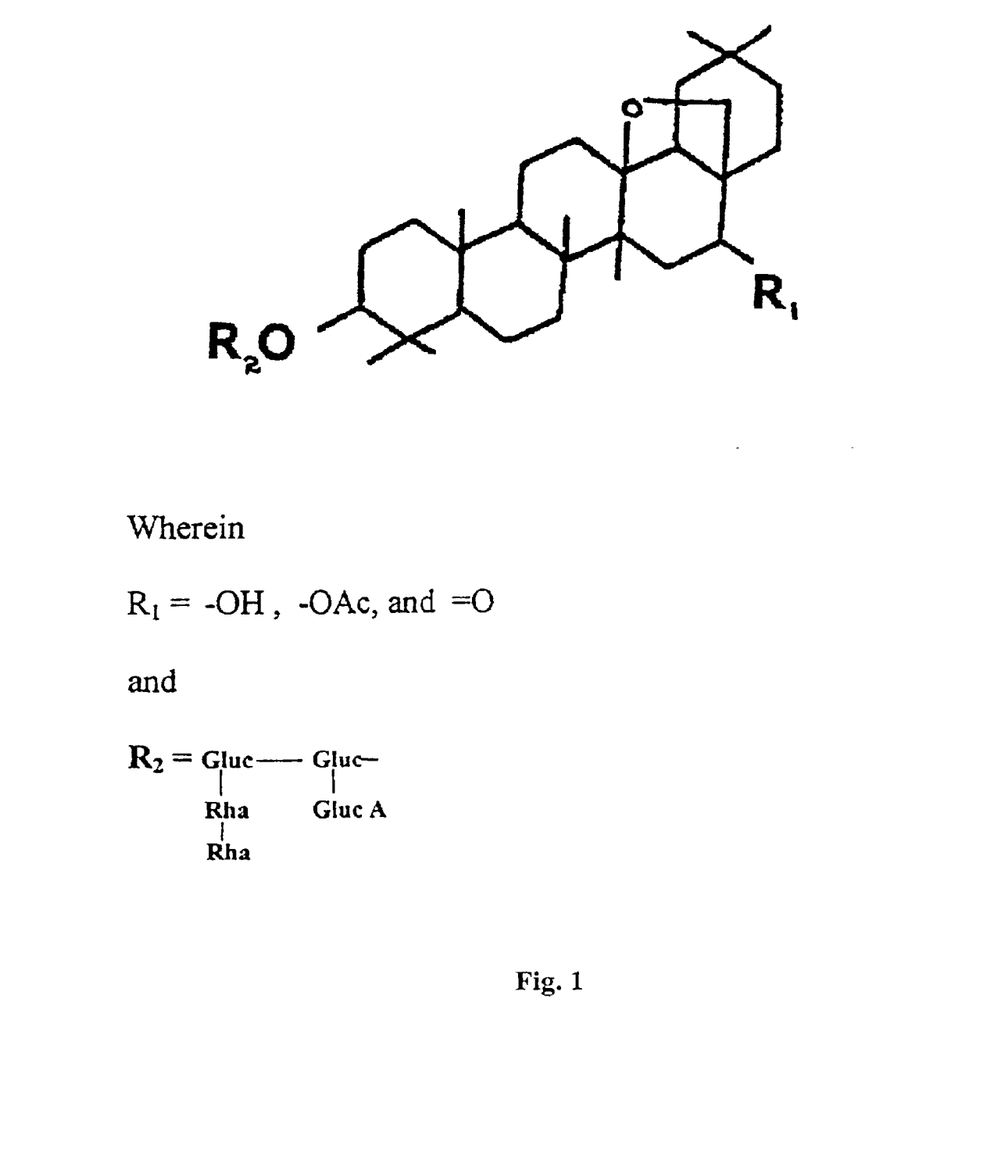
FIG. 1 shows the structure of the novel compound oleanane triterpenoid oligoglycoside isolated and identified from the active fraction of *Aegiceras corniculatum*.
Figure 2:
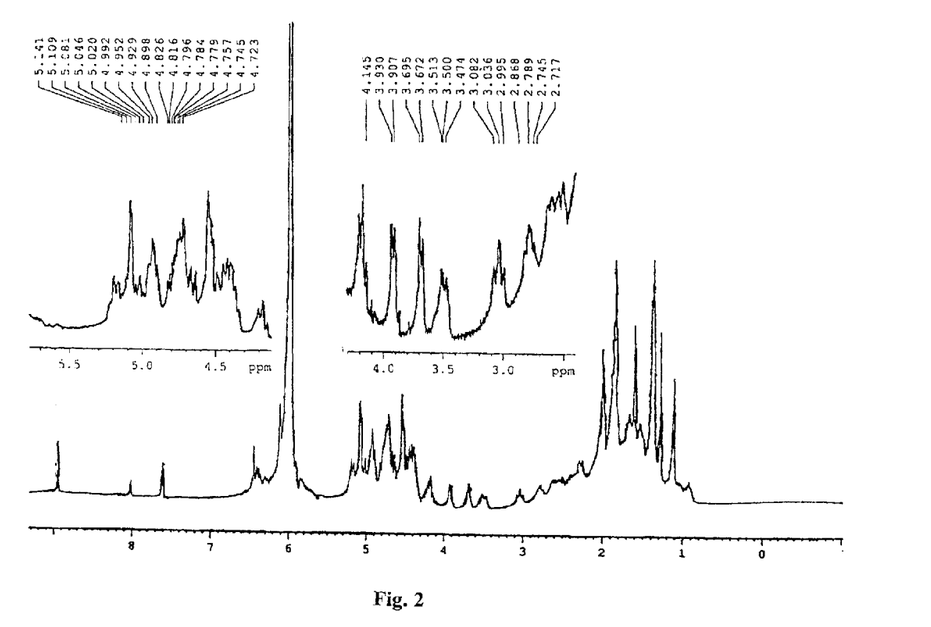
FIG. 2 shows the $^1H$ NMR spectrum in $C_5D_5N$ and DMSO.

The invention relates to a novel compound oleanane triterpenoid oligoglycoside of formula 1 of the accompanying drawing (trivially called corniculatonin). The invention also relates to a process for the isolation of the novel compound from a mangrove plant *Aegiceras corniculatum* (Blanco) belonging to the family Myrsinaceae. It also discloses the antifungal properties of the said compound. The invention further relates to the use of the said compound as a food preservative.

BACKGROUND OF INVENTION

Aspergillus sp. and many other moulds are often common contaminants of food, and effect the quality of the contaminated food by reducing starch and fat contents and lowering digestible energy level (William K. C., Blaney B. J. The potential of mould to reduce the value of foodstuffs. Proceeding of the aquaculture nutrition workshop. Allan G L, Dall W. Eds. Salmadar Bay, NSW-Australia. NSW. Fisher's 1992, 205–213). Aspergilli are known to occur on cereals, treenuts, peanuts, cotton, fruits, meat, poultry and sea food products (Jay J. M. 1978. Modem food microbiology, sec. Eds. D. Van Norstrand Company, New York.). *Aspergillus fresenii* and *A. niger*, used in the present investigation were found to be commonly associated with food products of wheat in coastal regions of India having warm and humid climate. The fungi from the genera Aspergillus are known to produce mycotoxins such as aflatoxins, fumronosins, fusaric acid, TA/AAL toxins, zearalenone, and trichothecene, 5-butyl picolinic acid and related phytotoxic pyridine derivatives. These mycotoxins are highly toxic to a variety of species including plants and humans and can be found in commercially prepared foodstuffs including milk and milk products, beans, cereals, sweet potatoes and commercially prepared animal feeds.

It is evident that new methods and formulations are needed to control plant and animal pathogens and the level of toxic metabolites present in consumable product and in the environment in general. The widespread use of pesticides, fungicides and chemical preservatives, however, has resulted in the development and evolution of resistant pathogens. As environment and health care concerns continue to mount, it will be necessary to identify or develop new fungicides to meet the environmental standards of the future. Particularly those, which are natural products for consumption by animals and thus have, low animal and environmental toxicities.

During the applicant's search for biologically active molecules from marine organism of Indian Ocean region, crude methanolic extract of a mangrove plant, *A. corniculatum* exhibited promising central nervous system depressant activity. In order to simplify the procedure for the isolation of the active principle, the crude extract was fractionated. The aqueous fraction being the major fraction, excess was left at room temperature. Surprisingly, it was observed that even on prolonged standing there was no fungal growth on the surface of the aqueous fraction. This indicated that the fraction must contain some molecule acting as antifungal agent. This observation coupled with the facts of increase in antibiotic resistant microbes and paucity of effective antifungals indicated a need for new antimycotic agents. It is with this goal in mind that the applicants studied the a aqueous fraction leading to the isolation of an active saponin.

Saponins are steroid or triterpenoid glycosides widely distributed in plants. The saponins have diverse biological activities finding use in agents employed as fungicides, insecticides, anticancer agents, cosmetics, food preservatives and fertilizers with growth promoting effects. Further use for saponins is in the removal of cholesterol from dairy products and as feed supplements for livestock such as chickens to reduce cholesterol levels in eggs.

A food preservative is containing saponin from aloe woods and p-hydroxy benzoic ester is disclosed in Japanese patent application no. 05009123. An antifungal drug containing saponin extracts from asparagus is described in Japanese patent application no. 2157205. The antimicrobial and pest activity of a saponin isolated from fruit pulp, tobacco and seed are described by Okunji et at. (Int. J. Crude Drug Res., 1990, 28:193–199); Gruenweller et al. (Phytochem., 1990, 29:2485–2490) and by Lalithat et al. (Int. Pest Control, 1988, 30:42–45) respectively. U.S. Pat. No. 4,477,361 (Sperti G. S. et al., 1984) describes a cinnamic compound containing an antimicrobial surfactant which is rendered substantive to the surface being washed. Film forming and/or anti-transpirants coating polymers such as NaHCO3 and light paraffinic petroleum oils have been reported to control the level of fungal colonization (Horst. et al. Plant Disease, 1992, 247–251; Elad et al. Phytoparasitica, 1989, 17:279–288 and Ziv, et al. Hort. Science, 1993,124).

Triterpene sapogenins from the bark of *Aegiceras majus* (Gaerten) (Syn. *Aegiceras corniculatum*) have been investigated by Rao and Bose, who initially reported isolation of aegiceradienol (Science and Culture, 1958, 24:486), genin A (Rao K. V. et al., J. Ind. Chem. Soc., 1959, 36:358); aegiceradiol (Rao K. V. et al., Tetrahedron, 1962, 18:461) and norechinocystadienol (Rao K. V. et al., J. Org. Chem., 1962, 27:1470) as products of usual acid hydrolysis of saponin mixture. Aegicerin (Rao K. V., Tetrahedron, 1964, 20:973) is reported to be present in the non-glycosidic extract of the bark of *A. majus* (Gaerten). Later on Hensens and Lewis (Henses O. D. et al., Tetrahedron letters, 1965, 4639) demonstrated that aegicerdiol or aegiceradienol are artifacts formed during the usual fairly vigorous hydrolysis conditions used for the crude glycosides mixture.

Isorhamnetin, echinocystic acid and rapanone are also known to be constituents of *Aegiceras corniculatum* (Henses O. D. et al., Aust J. Chem., 1966, 19:169). This mangrove is known to photosynthesize aspartate and alanine as major products of short time photosynthesis (Bhosale L. et al., Photosynthetica, 1983, 17:59). Payne reports the presence of fish toxin, 5-O-methyl embelin in this mangrove (Payne A. M., Diss. Abst. Int. PT. B. Sci. and Eng. 1991, 51:225). Chattopadhyay et al, (Chattopadhyay S. et al., Proceedings of the National Symposium on Marine Resources, Techniques, Evaluation and Management; Vaidyanadhan R. et al., eds., 1990, 5–7) found lupeol, amyrin, oleanolic acid and ursolic acid besides campesterol, stigmasterol and sitosterol, to be the major triterpenoids and steroids respectively. Saponin fraction of *Anagallis arvensis* is antiviral being effective against Herpes simplex virus type I and polio virus (Amoros M et al., Ann. Pharm. Fr., 1977, 35:371; Pl. Med. Phytoh., 1979, 13:122 and Amoros M. et al., Phytochem, 1987, 26:787). Its crude glycoside, Heteroside I, wherein anagalligenone is the constituent genin is reported to be antifungal and to inhibit germination of linseed. Its $LD_{50}$ in mice was 675 mg/Kg per os and 30.4 mg/Kg by s.c.

(Staron T. et al., Phytiat-Phytopharm, 1969, 18:161). The saikosaponins of *Bupleurum falcatum*, a crude drug in oriental medicine for treatment of hepatobiliary and anti-inflammatory diseases, have shown several metabolic actions in rat, in addition to anti-inflammatory action (Yamamoto M. et al., Arzneim Forsch, 1975, 25:1021,1240).

A comparative study of saikosaponins of *Bupleurum longeradiatum* var. *breviradiatum* and *B. falcatum* showed that per os administration of 1.0–3.0 g/Kg of the saponin was non toxic and the analgesic effect of the former was twice that of later. Both (500 mg/Kg os) prolonged sleeping time produced by hexabarbital sodium in mice (Imaoka, I. et al., Shioku Igaku Zasshi, 1970, 26:1; Chem. Abstr., 1970, 73:43769).

Sakurasaponin from *Rapanea melanophloeos* (L.) Mez (Myrsinaceae) exhibits molluscidal at 3 ppm and antifungal against plant pathogenic fungus *Cladosporium cucumerinum* at 1 µg in TLC bioassay (Ohtani Kazuhiro et al., Phytochem, 1993, 33:83).

OBJECTS OF THE INVENTION

The main object of the present invention is to provide a novel compound oleanane triterpenoid oligoglycoside of formula 1 of the accompanying drawing.

Another object of the present invention is to provide a process for the isolation of the said compound from a mangrove plant *Aegiceras corniculatum* (Blanco), belonging to the family Myrsinaceae.

Still another object of the present invention is to study the anti-fungicidal property of the compound.

Yet another object of the present invention is to provide a composition containing the compound useful as fungicidal and food preservative.

SUMMARY OF THE INVENTION

The invention relates to a novel compound oleanane triterpenoid oligoglycoside of formula 1 of the accompanying drawing (trivially known as corniculatonin). The invention also provides a process for the preparation of the compound from a mangrove plant *Aegiceras corniculatum* (Blanco) belonging to family Myrsinaceae. The invention further provides a composition containing the compound useful as fungicidal and food preservative and a process for preparing the same.

DETAILED DESCRIPTION OF THE INVENTION

According to the invention there is provided, a novel compound oleanane triterpenoid oligoglycoside (trivially called corniculatonin) of formula 1 of the accompanying drawing, which is hereinafter described in detail. More particularly, this invention relates to the discovery of antifungal properties for a novel composition of corniculatonin, which has therefore been isolated from a mangrove *Aegiceras corniculatum* (Blanco). These properties include inhibition of the growth of the opportunistic fungi Candida sp. and *Cryptococcus neoformans* in the disc diffusion assays. In this assay, the compound of formula I of the accompanying drawings was fungicidal for Candida sp., *Cryptococcus neoformans*, *Microsporum gypseum*, *Trichophyton mentagrophytes*, *T. tonsurans*, *T. violaceum* and the food spoilage fungi *Aspergillus fresenii*. Except the two opportunistic fungi, other fungi tested are resistant to nystatin.

In fact, the invention relates to a novel antifungal composition with a novel compound oleanane triterpenoid oligoglycoside, named as corniculatonin of formula 1 of the accompanying drawing, derived from a mangrove plant, *Aegiceras corniculatum* (Blanco), belonging to family Myrsinaceae. The compound is endowed with a marked wide range of antimycotic activity. The activity was demonstrated by disc diffusion method and has been evaluated in vitro as MIC (minimum inhibition concentration) against the fungal strains of Candida sp., *Cryptococcus neoformans*, *Trichophyton mentagrophytes*, *T. tonsurans*, *T. violaceum*, *Microsporum gypseum* and against the mould *Aspergillus fresenii* and *A. niger*. The compound is effective in infections caused by Candida sp., *Cryptococcus neoformans*, *Trichophyton mentagrophytes*. *T. tonsuras*, *T. violaceum* and *Microsporum gypseum* and against the food spoilage mould *Aspergillus fresenii*. Amphotericin B and nystatin have been taken as reference compounds. The compound of formula 1 of the accompanying drawings is comparable in activity against yeast, *Cryptococcus neoformans* and Candida sp. one of the strains on which the compound acts are resistant to nystatin, which makes the compound a better candidate than the reference compound, nystatin. All the strains of fungi tested are sensitive to amphotericin B as well as the novel compound but the novel compound of formula 1 of the accompanying drawings is slightly less potent than the antibiotic.

In an embodiment of the invention, the present invention provides a novel compound oleanane triterpenoid oligoglycoside of the formula 1 of the accompanying drawing (trivially called corniculatonin) wherein $R_1$ is selected from the group comprising of $^-OH$, $^-OAc$ and $=O$; and $R_2$ is a carbohydrate moiety.

In another embodiment of the present invention, the $R_1$ can have α and β configuration.

In still another embodiment of the present invention, the carbohydrate is a polysaccharide with monosaccharide having D or L rotation and intersugar linkages have α and β configuration.

In yet another embodiment of the present invention, the carbohydrate is linked to an aglycone at position 3 and has β configuration.

In one more embodiment of the present invention, the carbohydrate moiety comprises of glucose, rhamnose and glucorinic acid.

In one another preferred embodiment of the present invention, $C_{13}$–$C_{28}$ oxydo ring has β configuration.

In an preferred embodiment of the present invention, the novel $R_2$ is

In an embodiment of the present invention, the compound inhibits the growth of the opportunistic fungi candida sp. and *Cryptococcus neoformans* in disc diffusion assays.

In another embodiment of the present invention, the compound inhibits growth of *Microsporum gypseum*, *Trichophyton mentagrophytes*, *T. tonsurans* and *T. violaceum*.

In still another embodiment of the present invention, the compound inhibits growth of *Aspergillus fresenii* and *A. niger*.

In yet another embodiment of the present invention, the compound is used for the treatment of candidiasis, cryptococcosis, epidermal infections and systemic infections.

In one more embodiment of the present invention, the compound is used as a food preservative.

The present invention also provides a process for the isolation of the compound oleanane triterpenoid oligoglycoside of formula 1 of the accompanying drawing, said process comprising contacting the plant parts with a organic solvent to obtain an extract; fractionating the extract by known methods; and isolating the compound from the fractionated extract by known methods.

In an preferred embodiment of the present invention, the process for the isolation of the compound comprises:

1. collecting and drying the plant parts of *Aegiceras corniculatum*;
2. immersing the plant parts in an organic polar solvent for a week;
3. filtering the extract to obtain a filtrate;
4. concentrating the filtrate by known methods;
5. treating the concentrate with polar solvents in increasing order of polarity to obtain different layers; and
6. subjecting the thus obtained layers to fractionation to get the compound.

In an embodiment of the present invention, the organic solvent is selected from the group comprising of ethyl acetate, methanol, heptane, hexane, isooctane, acetone, benzene, toluene, diethyl ether, methylene chloride, chloroform, butanol, ethanol, isopropanol, 1,2 dichloroethane and mixtures thereof.

In another embodiment of the present invention, the solvents are selected from the group comprising of ethyl acetate and methanol.

In still another embodiment of the present invention, the plant parts are selected from the group comprising of leaves, stems, branches and roots.

In yet another embodiment of the present invention, the fractionation is performed by column chromatography.

In one more embodiment of the present invention, the column chromatography is performed by XAD-2, Sephadex $LH_{20}$, and silica gel.

In one another embodiment of the present invention, the solvents used for eluting are selected from the group comprising of heptane, methanol, dichloromethane, ethyl acetate, hexane, isooctane, chloroform, 1,2 dichloroethane, benzene, toluene, isopropanol, butanol, water, ethanol, diethyl ether and mixtures thereof. Particularly preferred eluents are chloroform, methanol and mixtures thereof.

The present invention further provides a composition having an effective amount of the compound oleanane triterpenoid oligoglycoside of formula 1 of the accompanying drawing optionally along with a pharmaceutically acceptable carrier.

In an embodiment of the present invention, the composition inhibits the growth of the opportunistic fungi candida sp. and *Cryptococcus neoformans* in disc diffusion assays.

In another embodiment of the present invention, the composition inhibits growth of *Microsporum gypseum, Trichophyton mentagrophytes, T. tonsurans* and *T. violaceum*.

In still another embodiment of the present invention, the composition inhibits growth of *Aspergillus fresenii* and *A. niger*.

In yet another embodiment of the present invention, the composition is used for the treatment of candidiasis, cryptococcosis, epidermal infections and systemic infections.

In one more embodiment of the present invention, the composition is used as a food preservative.

Further more, the present invention provides a method of treating fungal infections in mammals by administering an effective amount of compound of formula 1 of the accompanying drawing or the extract obtained from the mangrove plant *Aegiceras corniculatu*.

In an embodiment of the present invention, 6.25 μg to 50 μg/ml of the compound or the extract is administered to the subject.

In another embodiment of the present invention, the subject is a human being.

BRIEF DESCRIPTION OF THE ACCOMPANYING DRAWINGS

In the accompanying drawings.

The invention is further described in the examples which should not be construed to limit the scope of the present invention. In conjunction with the detailed and general description above, the examples provide further understanding of the present invention and outline a process for producing the composition of the invention.

EXAMPLES

Example 1

Preparation of Crude Extract

A 10 Kg (wet weight) sample of *Aegiceras corniculatum* (Blanco) collected from West Coast of India, was extracted by soaking in methanol for a week. After decanting the extract, the material was soaked in fresh methanol and extracted in the same manner. The combined extract was vacuum concentrated at 35° C. to obtain crude extract (256 gms). This example illustrates the methodology used for preparation of crude methanolic extract from *A. corniculatum*.

Example 2

Fractionation of Crude Extract

The methanolic extract was concentrated to about 500 ml of aqueous suspension and then fractionated into different fractions using solvents of increasing polarity. It was thus fractionated into chloroform, n-butanol and the aqueous residue fraction, n-Butanol and aqueous fractions were selected for follow up studies.

Example 3

Purification and Identification of Compound 1

Purification of the novel compound of formula 1 from the aqueous phase may be done by repeated column chromatography of the aqueous phase, first over XAD-2, followed by Sephadex $LH_{20}$. With XAD-2, the solid was loaded and eluted first with water and then with methanol whereas with Sephadex $LH_{20}$, the material was eluted with methanol. It was further purified by passing over silica gel (60–120 mesh) and elution with MeOH:CHCl3 (1:2).

The novel compound of formula 1, object of the present invention, was also found to be present in n-butanol fraction.

In chloroform:methanol:water (65:35:10) $R_f$ value is 0.56. The structure of the new compound was established on the basis of spectral data (Chart 1) to which trivial name corniculatonin 1 was proposed.

Corniculatonin 1 was isolated as a white powder. A molecular formula of C sub. 60 H sub. 98 O sub. 27 was deduced from detailed analysis of the sup. 13 C, sup. 1H NMR and high resolution FAB mass spectrum.

Compound of formula 1 gave positive Liebermann-Burchard test indicative of a triterpenoid. The IR spectrum showed absorption at 3410 cm$^{-1}$ for hydroxyl groups and at 1728 for carboxyl group of glucuronic acid. The sup. 1H NMR spectrum ($C_5D_5N$) revealed the presence of seven tertiary methyl groups at δ0.756, 0.95, 1.01, 1.04, 1.075, 1.29, 1.528 and a doublet at δ1.59 (J=5.4 Hz), assigned to the secondary methyl of deoxy sugars (rhamnose and fucose). In addition, there were peaks at δ3.51 (1H, d, J=6.9 Hz) and 3.28 (1H, d, J=6.9 Hz), suggesting the presence of 13,28 epoxide moiety as observed for 13,28 epoxy oleanane compound (Ahmad et al., Phytochem, 1988, 27:304). This was supported by the presence in its sup. 13C NMR spectrum of oxygenated quarternary carbon signal at δ86.7 and a triplet at triplet at δ77.7. 1H NMR was also available, in its downfield region of the presence of 5 anomeric proton signals at 4.1 (d, J=7.5 Hz); 4.7 (d, J=7.1 Hz); 5.19 (d, J=7.8 Hz); 5.97 (d, J=3.2 Hz) and 6.07 (d, J=3.5 Hz). Multiplets due to H-3 and H-16 were evident at δ3.14 and 4.05 respectively. Signal for H-16 proton overlapped due to severe spectral crowding in the region δ3.9–5 characteristic of oligosaccharides. The presence in the molecule of 5 sugar units was further confirmed by the presence of the signals in sup. 13C NMR at δ99.9, 100.4, 102, 103.2 and 104.6 The interglycosidic linkage as well as the position of attachment of the carbohydrate moiety to the aglycone was established by sup. 13 C NMR spectroscopy. The assignments of carbon resonances due to sugar moieties of 1 was carried out by comparison with those reported for the saccharide chain in triterpenoid saponin and by considering glycosidation effects (Agarwal P. K., Phytochem, 1992, 31:3367). The glycosidation shift of C-3 carbon signal from δ81.0 in the aglycone to δ90.8 in saponin disclosed that the carbohydrate moiety is located at C-3 of aglycone. Anomeric carbon resonances demonstrated that all the monosaccharide units are substituted at C-1. Thus the carbon chemical shifts of terminal glucoronic acid and rhamnose could be attributed. Sugar sequence in the molecule was established on the basis of its FAB mass spectrum in the negative mode. The mass spectrum showed peaks at m/z (rel. int. %) 1249 [M–H]$^-$, (100); 1103[M–Rha.]$^-$, (13); 1073 [M–GlucA]$^-$, (7.5); 957 [M–(Rha.+Rha.)]$^-$, (4.5); 795 [M–(Rha.+Rha.+Gluc.)]$^-$, (5). Simultaneous losses of fragment 146 (rhamnose), 176 (glucoronic acid) was indicative of two terminal sugars suggestive of two sites of attachment of a branched side chain. The +ve ionisation FABMS confirmed this results with peaks at m/z (rel. int. %) 1274[M+Na]$^+$ (100); 1128 [(M+Na)–Rha]$^+$ (8.8), 1098[(M+Na)–GlucA]$^+$ (11); 982 [(M+Na)–(Rha.+Rha)]+ (4). The fragment at m/z 815 corresponded to [(M$^+$+Na)–glycone]$^+$. This fragmentation corresponded to the subsequent losses from the molecular ion peaks of rhamnose, rhamnose, glucose and glucuronic acid. Based on this data it was evident that the preferred compound is a new saponin identified as 3-O-α-rhamnopyranosyl-rhamnopyranosyl-glucopyranosyl-glucoronopyranosylgluco-pyrano side 16 α-hydroxy-13,28-epoxy oleanane to which the applicants have also proposed the trivial name corniculatonin.

Figure 3:
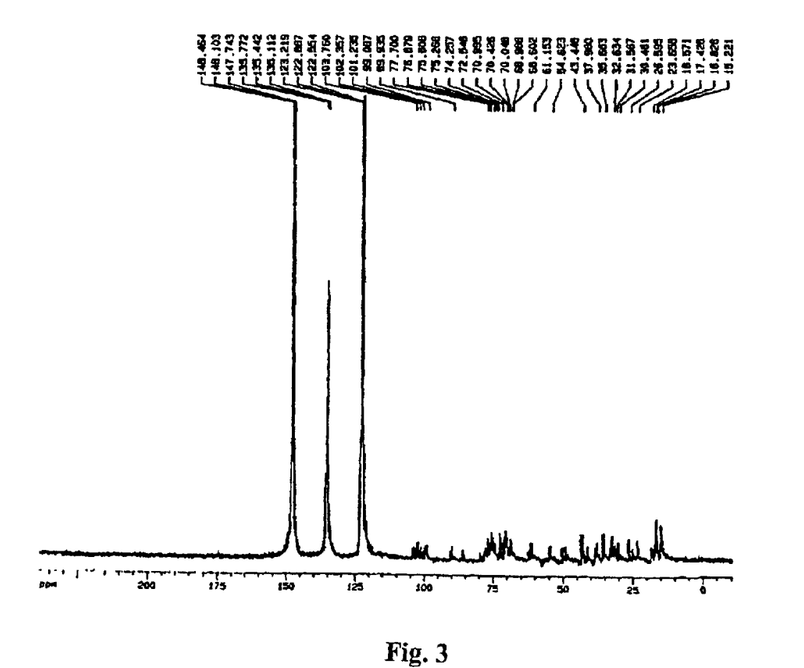
FIG. 3 shows the $^{13}C$ NMR and DEPT spectrum in $C_5D_5N$.
Figure 4:
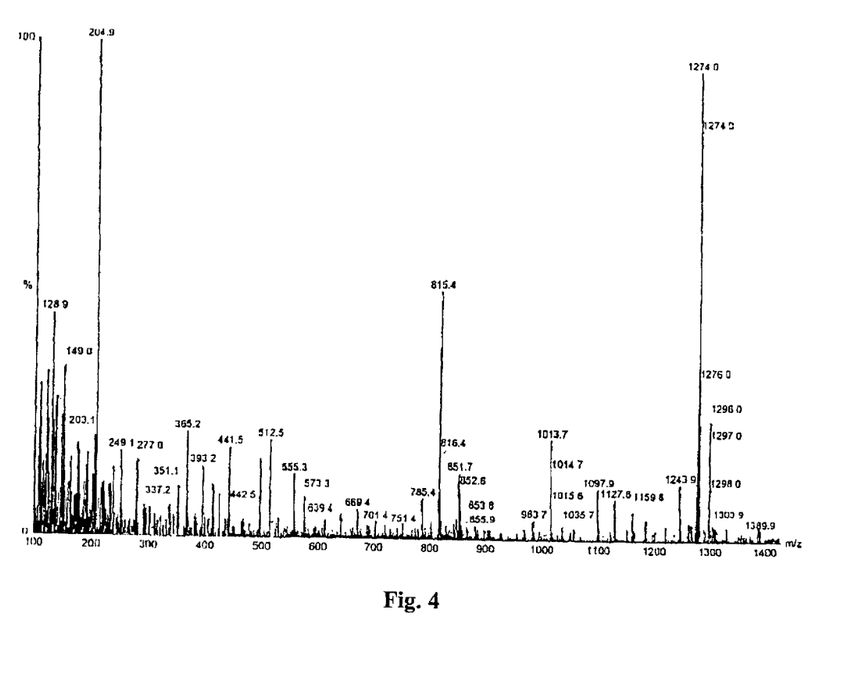
FIG. 4 shows FABMS of compound 1 in negative and positive mode.
Figure 5:
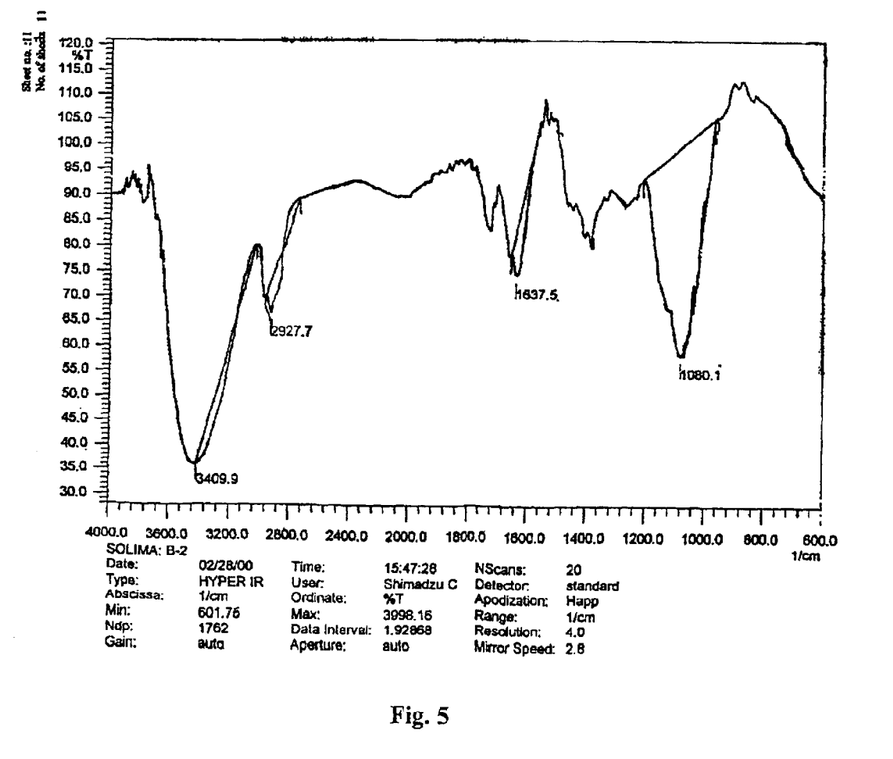
FIG. 5 shows IR spectrum of compound 1 (KBr).

SUP$^{13}$C NMR DATA OF COMPOUND 1 (CHART 1)

| C-1 | 39.0 | Sugars | | | |
|---|---|---|---|---|---|
| C-2 | 26.0 | C-1 | 103.2 | C-1"" | 102.4 |
| C-3 | 90.8 | C-2 | 75.2 | C-2"" | 72.0 |
| C-4 | 39.5 | C-3 | 76.5 | C-3"" | 71.3 |
| C-5 | 55.5 | C-4 | 73.4 | C-4"" | 73.4 |
| C-6 | 18.2 | C-5 | 76.7 | C-5"" | 69.4 |
| C-7 | 32.4 | C-6 | 175.0 | C-6"" | 17.9 |
| C-8 | 42.1 | C-1' | 104.6 | | |
| C-9 | 50.1 | C-2' | 79.0 | | |
| C-10 | 36.7 | C-3' | 76.7 | | |
| C-11 | 18.9 | C-4' | 71.8 | | |
| C-12 | 34.1 | C-5' | 80.4 | | |
| C-13 | 86.7 | C-6' | 62.9 | | |
| C-14 | 44.3 | C-1" | 100.4 | | |
| C-15 | 36.5 | C-2" | 75.5 | | |
| C-16 | 78.5 | C-3" | 77.5 | | |
| C-17 | 44.3 | C-4" | 70.05 | | |
| C-18 | 51.2 | C-5" | 75.9 | | |
| C-19 | 38.8 | C-6" | 62.0 | | |
| C-20 | 36.7 | C-1''' | 99.9 | | |
| C-21 | 31.5 | C-2''' | 75.5 | | |
| C-22 | 36.5 | C-3''' | 75.6 | | |
| C-23 | 27.4 | C-4''' | 74.2 | | |
| C-24 | 16.16 | C-5''' | 69.8 | | |
| C-25 | 16.16 | C-6''' | 17.7 | | |
| C-26 | 18.9 | | | | |
| C-27 | 19.4 | | | | |
| C-28 | 77.7 | | | | |
| C-29 | 33.5 | | | | |
| C-30 | 24.5 | | | | |

Example 4

Antifungal Activity of the Composition of the Invention

The following assay method was utilized to demonstrate in vitro antifungal effectiveness of composition of the invention as reported in Tables 1 and 2.

Example 5

Materials and Methods

Agar: Czapek Malt Agar (Himedia laboratories Ltd.) was used for culturing *Microsporumn gypseum, Trichophyton mentagrophytes T. tonsurans, T. violaceum, Aspergillus fresenii* and *A. niger*. Mycological Agar (Himedia Laboratories Ltd) was used for *Cryptococcus neoformans* and Candida sp.

Example 6

Reference Compounds

Amphotericin B and Nystatin (Himedia laboratories Ltd.) were used as standards for comparison.

Example 7

Fungal Strains

Pathogenic fungal strains of yeast and filamentous fungi identified and gifted by Dr. Savio from Goa Medical College, Bambolim, were used for the test. Strains of Aspergillus were isolated from the infected wheat bread with sterile needle; fungal material was surface sterilized using 0.5% sodium hypochlorite for 2–3 minutes, and then washed with small brush in sterile distilled water. Washed fungal material was transferred using needle into the sterile culture media and subcultured for purification by following standard methods (Collins and Taylor, 1967). Taxonomic identification was done by using various standard keys (Ainswort et al., 1973; Onion et al., 1981) and identification confirmed by Alka Pandey of Agarkar Research Institute, Pune.

Example 8
Preservation of Fungal Strains

Yeast strains (Candida sp. and *Cryptococcus neoformans*) were maintained by single colony transfer on mycological agar (Himedia Laboratories Ltd) at the refrigeration temperature (3–5° C.) Filamentous fungi were maintained on Czapek Malt slants at refrigeration temperature (3–5° C.), until needed for the assay.

Example 9
Assay Protocols

Disk diffusion assay: The disk diffusion assay was used for screening of antifungal activity of the compound. The stock solution for the test was prepared by dissolving 5 mg of the compound of formula 1 in 200 μl dimethylsulfoxide (DMSO). From the stock solution 10 μl were spread on the paper disc so as to obtain the final concentration of 250 μg disk$^{-1}$ Control disk was applied reconstituted with only dimethylsulphoxide and were dried at 28–29° C. Completely dried disk was applied to innoculated plates. The plates were incubated at room temperature for the period between 42–120 hrs. to obtain maximum growth in the culture media. The zones of inhibition around the disks were measured. The results obtained in these bioassays are summarized in Table 1.

TABLE 1

Preliminary antifungal activity of compound of formula 1 from *A. corniculatum*

| Microorganism used | Disk Diffusion Method |
|---|---|
| | Compound 1 250 μg. disk$^{-1}$ |
| *Trichophyton mentagrophytes* | 12 mm |
| *T. tonsurans* | 14 mm |
| *T. violaceum* | 13 mm |
| Cryptococcus Neofonnans | 9 mm |
| Candida sp. | 9 mm |
| Microsporum Gypseum | 14 mm |
| *Aspergillus fresenii* | 10 mm |
| *Aspergillus niger* | 4 mm |

Minimum Inhibitory Concentration (MIC)

Innocula were adjusted to 100 μl of *Cryptococcus neoformans*, Candida sp., *Microsporum gypseum, Trichophyton tonsurans, T. violaceum* and *Trichophyton mentagrophytes* and spread on the appropriate plates, excess moisture was allowed to absorb for 10 minutes before applying disks. Immediately prior to the assay, the testing compound of formula 1, object of the present invention, the reference compounds amphotericin B and nystatin, potency approx:750 μ/mg and 480 USP unit/mg respectively, were reconstituted in triplicate in dimethylsulfoxide. The stock solution for the MIC was prepared by dissolving 1 mg, 0.5 mg, and 0.25 mg in 200 μl of dimethylsulfoxide (DMSO) and 0.625 mg, 0.312 mg in 1 ml of dimethylsulfoxide (DMSO). From the stock solution 10 μl were spread on the paper disk so as to obtain final concentration of 50 μg disc$^{-1}$, 25 μg disc$^{-1}$, 12.5 μg disc$^{-1}$, 6.25 μg disc$^{-1}$ and 3.12 μg disk$^{-1}$. Disks were dried at reduced pressure in the dessicator, at 28–29° C. and applied to innoculated plates. Test plates were incubated for 42–120 hrs at room temperature to obtain maximum growth and MIC was determined as lowest concentration of compound and antifungal agents resulting in a clear zone of growth inhibition.

In testing, the compound of formula 1 was reconstituted in dimethylsulfoxide (DMSO) immediately prior to all assays. Dimethylsulfoxide (DMSO) alone had no detectable inhibitory effect on any of the tested microbes. Compound of formula 1 was tested against a diverse collection of yeast and filamentous fungi, some of which are resistant to the reference compound nystatin. Filamentous fungi were nystatin resistant.

The in vitro antifungal activity of compound of formula 1, object of the present invention, in disk diffusion method is summarized in Table 2, below:

TABLE 2

MIC (μg/disk$^{-1}$) for Antifungal Activity of compound of formula 1 from *A. corniculatum*

| | Disk Diffusion Method | | |
|---|---|---|---|
| Microorganism used | Compound 1 μg. disk$^{-1}$ | Amphotericin B μg. disk$^{-1}$ | Nystatin μg. disk$^{-1}$ |
| Trichophyton Mentagrophyres | 25–50 | 6.25–12.5 | — |
| *T. tonsurans* | 12.5–25 | 6.25–12.5 | — |
| *T. violaceum* | 25–50 | 6.25–12.5 | — |
| Cryptococcus Neoformans | 6.25–12.5 | 3.12–6.25 | 6.25–12.5 |
| Candida sp. | 6.25–12.5 | 3.12–6.25 | 6.25–12.5 |
| Microsporum Gypseum | 12.5–25 | 6.25–12.5 | — |
| *Aspergillus fresenii* | 25–50 | 12.5–25 | — |
| *Aspergillus niger* | — | 12.5–25 | — |

It is evident from the above Table 2 that the compound of formula 1 was fungicidal against all the strains of yeast and filamentous fungi tested except *Aspergillus niger*. It is comparable to the reference compound nystatin against yeast *Cryptococcus neoformans* and Candida sp. in activity and active even against the nystatin resistant filamentous fungi which makes the novel composition of formula 1 a better candidate than the reference compound, nystatin. The novel composition of formula 1 is slightly less potent than the antibiotic amphotericin B against the fungi examined. All the strains of fungi tested are sensitive to amphotericin B.

Based upon the foregoing observation, this compound of formula 1, object of the present invention, is believed to be useful in the treatment of one or more fungal infections such as aspergillosis, candidiasis, internal infections such as cryptococcosis, epidermal infections caused by antibiotic resistant fungi and the like. It may also be useful as a food preservative.

The scope of the present invention is not limited by the description, examples and suggested uses herein and modification can be made without departing from the spirit of the invention. The compound described herein may have other useful application. therapeutic application of the compound of formula 1, of the present invention, can be accomplished by the suitable therapeutic method and techniques as presently or prospectively known to those skilled in the art. Further, the compound of the invention may have use as a starting material for the preparation of other useful compounds. Thus, it is intended that the present invention covers the modification and variation of this invention provided that, they are within the scope of the appended claims and their equivalents.

What is claimed is:

1. An oleanane triterpenoid oligoglycoside isolated from *Aegiceras corniculatum* and having the formula I:

wherein $R_1$ is selected from the group consisting —OH, —OAc and =O.

2. The isolated oleanane triterpenoid oligoglycoside compound according to claim 1 wherein $R_1$ has α or β configuration.

3. The isolated oleanane triterpenoid oligoglycoside compound according to claim 1 wherein the polysaccharide carbohydrate portion has a monosaccharide having D or L rotation and the intersugar linkages have α or β configuration.

4. The isolated oleanane triterpenoid oligoglycoside compound according to claim 1 wherein the carbohydrate portion linked to the alglycone portion at position 3 has a β configuration.

5. The isolated oleanane triterpenoid oligoglycoside compound according to claim 1 wherein $R_1$ is —OH.

6. The isolated oleanane triterpenoid oligoglycoside compound according to claim 1 wherein the $C_{13}$–$C_{28}$ oxydo ring has a β configuration.

7. The isolated oleanane triterpenoid oligoglycoside compound according t claim 1 wherein the compound inhibits growth of fungi selected from candida sp. and *Cryptococcus neoformans*.

8. The isolated oleanane triterpenoid oligoglycoside compound according to claim 1 wherein the compound inhibits growth of *Microsporin gypseum, Trichopyton mentagrophytes, T. tonsurans* and *T. violaceum*.

9. The isolated oleanane triterpenoid of oligoglycoside compound according to claim 1 wherein the compound inhibits growth of *Aspergillus fresenii* and *A. niger*.

10. The isolated oleanane triterpenoid oligoglycoside compound according to claim 1 wherein the compound is used for treating candidiasis, cryptococcosis, epidermal infections and systemic infections.

11. The isolated oleanane triterpenoid oligoglycoside compound according to claim 1 the compound is used as a food preservative.

* * * * *